(12) United States Patent
Bergendahl et al.

(10) Patent No.: US 10,109,455 B2
(45) Date of Patent: Oct. 23, 2018

(54) SYSTEM AND METHOD FOR PERFORMING NANO BEAM DIFFRACTION ANALYSIS

(71) Applicant: International Business Machines Corporation, Armonk, NY (US)

(72) Inventors: Marc Adam Bergendahl, Troy, NY (US); James John Demarest, Rensselaer, NY (US); Christopher J. Penny, Saratoga Springs, NY (US); Roger Allen Quon, Rhinebeck, NY (US); Christopher Joseph Waskiewicz, Rexford, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 15/908,400

(22) Filed: Feb. 28, 2018

(65) Prior Publication Data

US 2018/0190470 A1     Jul. 5, 2018

Related U.S. Application Data

(63) Continuation of application No. 15/199,350, filed on Jun. 30, 2016.

(51) Int. Cl.
*H01J 37/26* (2006.01)
*H01J 37/28* (2006.01)

(52) U.S. Cl.
CPC .......... *H01J 37/261* (2013.01); *H01J 37/28* (2013.01); *H01J 2237/206* (2013.01); *H01J 2237/2802* (2013.01); *H01J 2237/3114* (2013.01)

(58) Field of Classification Search
USPC ........................................ 250/311, 307, 306
See application file for complete search history.

(56) References Cited

U.S. PATENT DOCUMENTS

| | | |
|---|---|---|
| 8,134,124 B2 | 3/2012 | Blackwood et al. |
| 8,399,831 B2 | 3/2013 | Faber et al. |
| 8,835,845 B2 | 9/2014 | Hong |
| 8,853,805 B2 | 10/2014 | Chung et al. |
| 9,057,670 B2 | 6/2015 | Demarest et al. |
| 2005/0082478 A1* | 4/2005 | Tanaka ................. G01N 23/225 250/311 |
| 2009/0166535 A1* | 7/2009 | Kim ....................... G01N 23/04 250/307 |
| 2014/0061032 A1 | 3/2014 | Miller et al. |

(Continued)

FOREIGN PATENT DOCUMENTS

WO     WO 2013/134680 A1     9/2013

OTHER PUBLICATIONS

H. Seitz et al., "Sensitivity Limits of Strain Mapping Procedures Using High-Resolution Electron Microscopy," Journal of Microscopy, vol. 190, No. 1-2, 1998, pp. 184-189.

(Continued)

*Primary Examiner* — Kiet T Nguyen
(74) *Attorney, Agent, or Firm* — Vazken Alexanian; McGinn IP Law Group, PLLC

(57) ABSTRACT

A system for performing diffraction analysis, includes a focused ion beam (FIB) device for preparing a sample, a mill for removing a surface portion of the prepared sample, and an analyzer for performing diffraction analysis on the milled sample.

20 Claims, 9 Drawing Sheets

(56) References Cited

U.S. PATENT DOCUMENTS

2015/0076346 A1 3/2015 Weiss
2016/0356729 A1* 12/2016 Bauer .................... H01J 37/20

OTHER PUBLICATIONS

V. B. Özdöl, "TEM for Strain-Engineered Devices," G.I.T. Imaging & Microscopy, vol. 14, Aug. 2012, pp. 18-20.
C. T. Koch et al., "An Efficient, Simple, and Precise Way to Map Strain with Nanometer Resolution in Semiconductor Devices," Applied Physics Letters, vol. 96, No. 9, 2010, 091901, 3 pages.

* cited by examiner

600

SYSTEM AND METHOD FOR PERFORMING NANO BEAM DIFFRACTION ANALYSIS

The present Application is a Continuation Application of U.S. patent application Ser. No. 15/199,350, which was filed on Jun. 30, 2016.

BACKGROUND OF THE INVENTION

Field of the Invention

The present invention relates to a system and method for performing nano beam diffraction (NBD) analysis and, more particularly to a system and method of performing NBD analysis which includes additional thinning of a focused ion beam (FIB) prepared transmission electron microscopy (TEM) sample. The additional milling is done to remove a damaged portion of the TEM sample.

Description of the Related Art

Convergent beam electron diffraction (CBED), nano beam electron diffraction (NBD), dark field holography, and experimental/modeling electron diffraction contrast imaging (EDCI) techniques are all valid ways to measure strain in single crystalline materials such as those found in semiconductor devices.

Of these, NBD has become one of the preferred methods for performing this type of analysis due to its relative ease of use and relatively straight forward interpretation. At NBD's fundamental level it looks at relative changes in atomic planes in a single crystalline material by looking at the displacement of diffraction spots in diffraction patterns compared to a reference pattern.

The spacing between the diffraction spots in a diffraction pattern directly correlate to the spacing between crystallographic planes in the crystalline material generating the pattern. The reference diffraction pattern is typically obtained from an unstrained region within the sample. It is then straightforward to calculate the strain (or lattice mismatch if multiple single crystalline materials are involved) of all the other diffraction patterns with respect to the reference where strain (ε) is:

$$\varepsilon = \Delta L/L_0 = (L_1 - L_0)/L_0$$

where $L_0$ is the distance between the diffraction spot of interest and the directly transmitted spot in the reference diffraction pattern, $L_1$ is the distance between the diffraction spot of interest and the directly transmitted spot in the experimental diffraction pattern, and $\Delta L$ is the difference between $L_1$ and $L_0$.

FIG. 1 illustrates a related art system 100 for performing nano beam diffraction (NBD) analysis.

As illustrated in FIG. 1, the system 100 includes a dual beam focused ion beam (DBFIB) device 110 for preparing a transmission electron microscopy (TEM) sample extracted from a structure (e.g., a semiconductor structure), and a TEM/NBD device 120 for performing NBD analysis on the TEM sample to acquire diffraction data.

The DBFIB device 110 can obtain a parallel-sided sample from a semiconductor wafer. This specimen geometry removes thickness variations contained within the sample.

The TEM/NBD device 120 may obtain strain data with about 5 nm spatial resolution and a 0.1% strain sensitivity.

SUMMARY

In view of the foregoing and other problems, disadvantages, and drawbacks of the aforementioned conventional devices and methods, an exemplary aspect of the present invention is directed to a system and method of performing nano beam diffraction (NBD) analysis which may provide diffraction data having a sensitivity which is less than 0.1%.

An exemplary aspect of the present invention is directed to a system for performing nano beam diffraction (NBD) analysis, including a focused ion beam (FIB) device for preparing a transmission electron microscopy (TEM) sample, a broad beam ion mill for milling the TEM sample to remove a surface portion of the TEM sample, and a strain analyzer for performing NBD analysis on the milled TEM sample to acquire diffraction data.

Another exemplary aspect of the present invention is directed to a method of performing nano beam diffraction (NBD) analysis, including preparing a transmission electron microscopy (TEM) sample, milling the TEM sample to remove a surface portion of the TEM sample, and performing NBD analysis on the milled TEM sample to acquire diffraction data.

Another exemplary aspect of the present invention is directed to a system for performing nano beam diffraction (NBD) analysis, including a focused ion beam (FIB) device for preparing a parallel-sided transmission electron microscopy (TEM) sample, a broad beam ion mill for milling the TEM sample to remove a surface portion from two parallel sides of the parallel-sided TEM sample which has been damaged by the FIB device and expose an underlying surface, the removed surface portion of the TEM sample can range in thickness from 1 nm to 45 nm, and a strain analyzer for performing NBD analysis on the milled TEM sample to acquire diffraction data on the underlying surface, ideally the strain analyzer using a TEM camera image resolution of at least 4000×4000 pixels to acquire the diffraction data (although it could be as few as 250×250 pixels), such that the diffraction data comprises a sensitivity which is less than 0.1%.

Another exemplary aspect of the present invention is directed to a method of performing nano beam diffraction (NBD) analysis, including preparing a parallel-sided FIB transmission electron microscopy (TEM) sample, further milling the TEM sample to remove a surface portion from two parallel sides of the parallel-sided TEM sample which has been damaged by the preparing of the FIB TEM sample and expose an underlying surface, the removed surface portion comprising a thickness in a range from 1 nm to 45 nm, and performing NBD analysis on the milled TEM sample to acquire diffraction data on the underlying surface, by using a TEM camera image resolution of at least 4000× 4000 pixels, such that the diffraction data comprises a sensitivity which is less than 0.1%.

Another exemplary aspect of the present invention is directed to a method of performing strain analysis. The method includes performing a first NBD analysis on a milled TEM sample from a strained region of a structure to acquire diffraction data, performing a second NBD analysis on a milled reference TEM sample from an unstrained region of the structure to acquire reference diffraction data, and comparing the diffraction data from the first NBD analysis with the reference diffraction data from the second NBD analysis to determine an amount of strain in the milled TEM sample. With its unique and novel features, the present invention provides a system and method of performing nano beam diffraction (NBD) analysis which may provide diffraction data having a sensitivity which is less than 0.1%.

BRIEF DESCRIPTION OF THE DRAWINGS

The foregoing and other objects, aspects and advantages will be better understood from the following detailed description of the embodiments of the invention with reference to the drawings, in which.

DETAILED DESCRIPTION OF THE EXEMPLARY EMBODIMENTS OF THE INVENTION

Figure 1:
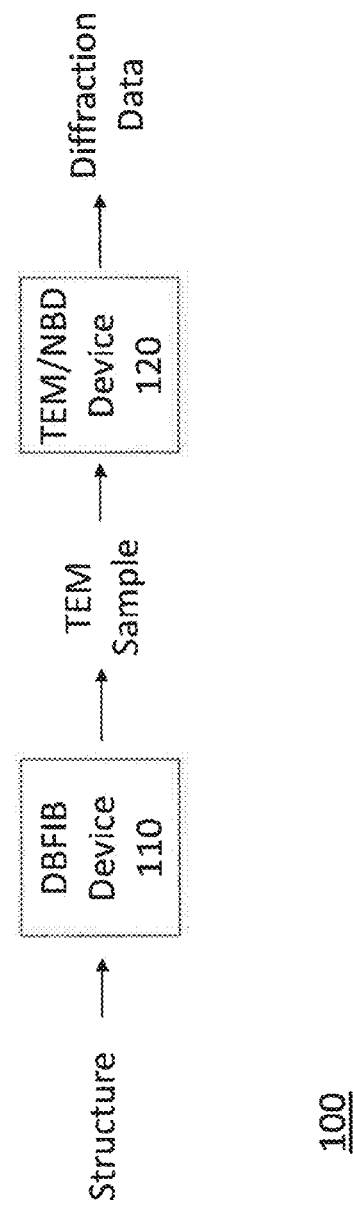
FIG. 1 illustrates a related art system 100 for performing nano beam diffraction (NBD) analysis.

Referring now to the drawings, FIGS. 2-9 illustrate the exemplary aspects of the present invention.

With the continual reduction in semiconductor device dimensionality, the shift to three dimensional device geometries (finFETs), and the introduction of new materials (SiGe), strain engineering of semiconductor structures has become a valid method of architecting device electrical performance. Strain engineering in semiconductor devices is typically on the order of 1-2%. However, some research devices are looking to engineer strain in structures at less than 1%.

This has placed a demand on characterization techniques to provide strain information with a spatial resolution on the order of nanometers and a strain sensitivity of less than 0.1%. Thus, it is desired to manufacture a transmission electron microscopy (TEM) sample with increased nanobeam diffraction (NBD) sensitivity of less than 0.1%. In particular, it would be useful if improvements in sensitivity could be obtained while preserving the current TEM sample preparation process.

Precession electron diffraction (PED) TEM techniques may be able to achieve better sensitivity than conventional TEM NBD analyses, but these techniques require additional hardware and software on a TEM.

Further, related art systems and methods such as the related art system in FIG. 1 (e.g., conventional FIB prepared samples), cannot provide strain sensitivity much less than 0.1%. This limit on sensitivity is due to several factors including the damage to the TEM sample surfaces caused by the conventional FIB (e.g., DBFIB) TEM sample preparation.

The layer of damage to the surface of TEM samples which is caused by FIB is proportional in depth into the sample to the accelerating voltage of the incident gallium (Ga) ions. This relationship is about 1 nm per kV.

It is common practice to finish a TEM sample with 2-5 kV Ga ions and strain samples are typically around 100 nm thick. As a result, about 5-10% of the final sample thickness is structurally damaged—the crystalline lattice of the materials in the sample has been amorphized or otherwise distorted. These damage layers may introduce a subtle artifact into the NBD patterns which worsen the sensitivity of the technique.

The inventors have discovered that it may be possible to improve the NBD strain sensitivity to be less than 0.1%, by removing the damage layers on the sample by preparing the TEM sample (e.g., by an in-situ method) in the FIB and subsequently removing a surface portion of the TEM sample (e.g., the Ga damaged material) with a broad beam (e.g., about 1 μm) ion beam in another sample preparation tool.

Thus, an exemplary aspect of the present invention may apply a broad beam ion mill after conventional FIB preparation to remove that damaged layer on the surface of the specimen, to improve the NBD strain sensitivity. This exemplary aspect may overcome the deficiencies of the related art systems and methods and achieve a strain sensitivity by NBD on the order of 0.08 to 0.07% which represents a 15-20% improvement over the related art systems and methods.

Figure 2:
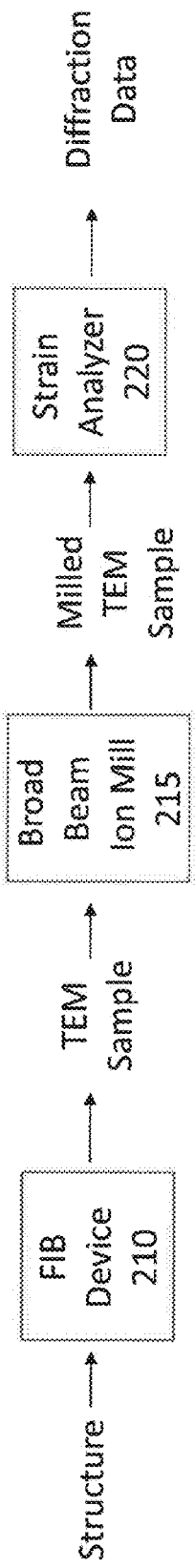
FIG. 2 illustrates a system 200 for performing nano beam diffraction (NBD) analysis, according to an exemplary aspect of the present invention.

FIG. 2 illustrates a system 200 for performing nano beam diffraction (NBD) analysis, according to an exemplary aspect of the present invention.

As illustrated in FIG. 2, the system 200 includes a focused ion beam (FIB) device 210 for preparing a transmission electron microscopy (TEM) sample, a broad beam ion mill 215 for milling the TEM sample to remove a surface portion of the TEM sample, and a strain analyzer 220 for performing NBD analysis on the milled TEM sample to acquire diffraction data.

Unlike the related art system 100 in FIG. 1 which performs NBD analysis on the TEM sample which has been damaged by the DBFIB 110, the system 200 mills the TEM sample to remove a surface portion (e.g., damaged layer) of the TEM sample and performs NBD analysis on the additionally milled TEM sample (e.g., on an underlying surface of the TEM sample which has been exposed by the milling).

Referring again to FIG. 2, the structure input to the FIB device (e.g., the structure to be analyzed) may include semiconductor structure such as a semiconductor wafer, a fin field effect transistor (finFET) and a vertical field effect transistor (vFET). In particular, the structure may include silicon, germanium, SiGe, etc.

The FIB device 210 may use a focused beam of ions (e.g., Ga ions) to mill (e.g., machine, cut, etc.) a TEM sample from the structure (e.g., semiconductor device). The FIB device 210 may include, for example, a dual beam FIB (DBFIB) which includes a scanning electron microscope (SEM) to view the TEM sample as the focused beam of ions mills the TEM sample from the structure.

For example, the FIB device 210 may include a gallium DBFIB tool used to mill and extract the TEM sample from the structure. The gallium DBFIB tool may generate an ion beam column based on setting an accelerating voltage in the range of about 0.5 kV to about 50 kV (typically 5 kV and 30 kV), an ion beam current in the range of about 1 pA to about 10 nA (typically 50 pA-9 nA), and a tilt angle in the range of about 0 to about 52 degrees (typically +/−2 degrees during TEM sample fabrication). The material sputter rate may vary according the ion beam current and accelerating voltage, as well as tool design and set up.

The electron beam column of the DBFIB tool may include an accelerating voltage in the range of about 0.5 kV-50 kV (typically 5 kV). The beam diameter of the ion beam may be about 1.0 nm to about 1000 nm, although small or larger beam diameters may be contemplated. Also, in operation, the ion beam may be rastered back and forth to cover an area which may be, for example, over 100 µm×100 µm.

Figure 3:
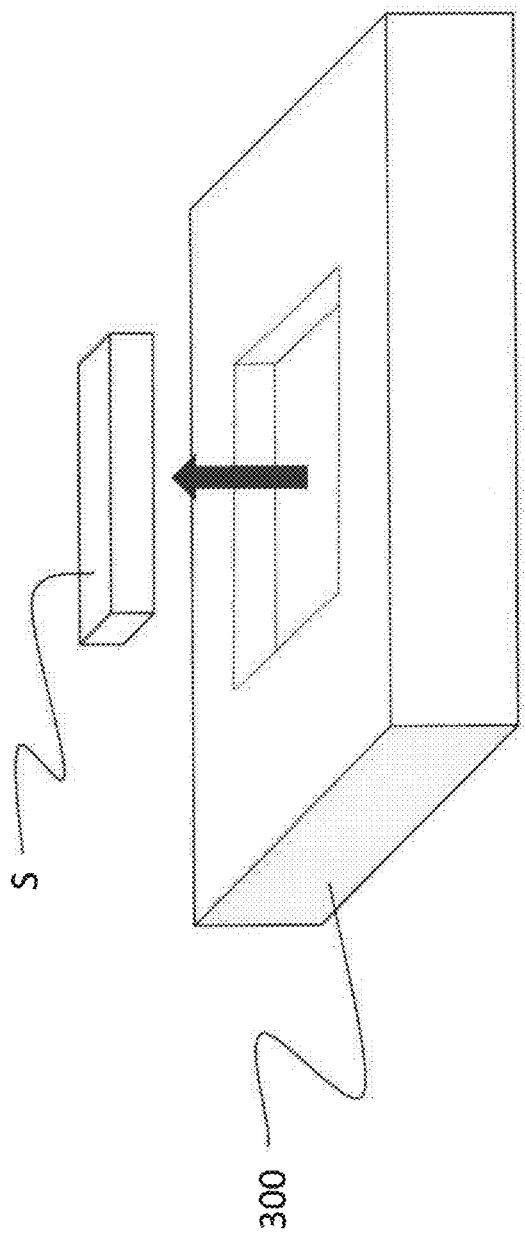
FIG. 3 illustrates a TEM sample S (e.g., parallel sided sample) which has been separated from the structure 300 (e.g., semiconductor device) by the FIB device 210, according to an exemplary aspect of the present invention.

FIG. 3 illustrates a TEM sample S (e.g., parallel sided sample) which has been extracted from the structure 300 (e.g., semiconductor device) by the FIB device 210, according to an exemplary aspect of the present invention. The TEM sample S may be machined from the structure by the FIB device 210 by using an in situ lift-out technique, or by some other technique (e.g., H-bar technique, ex situ technique).

Figure 4:
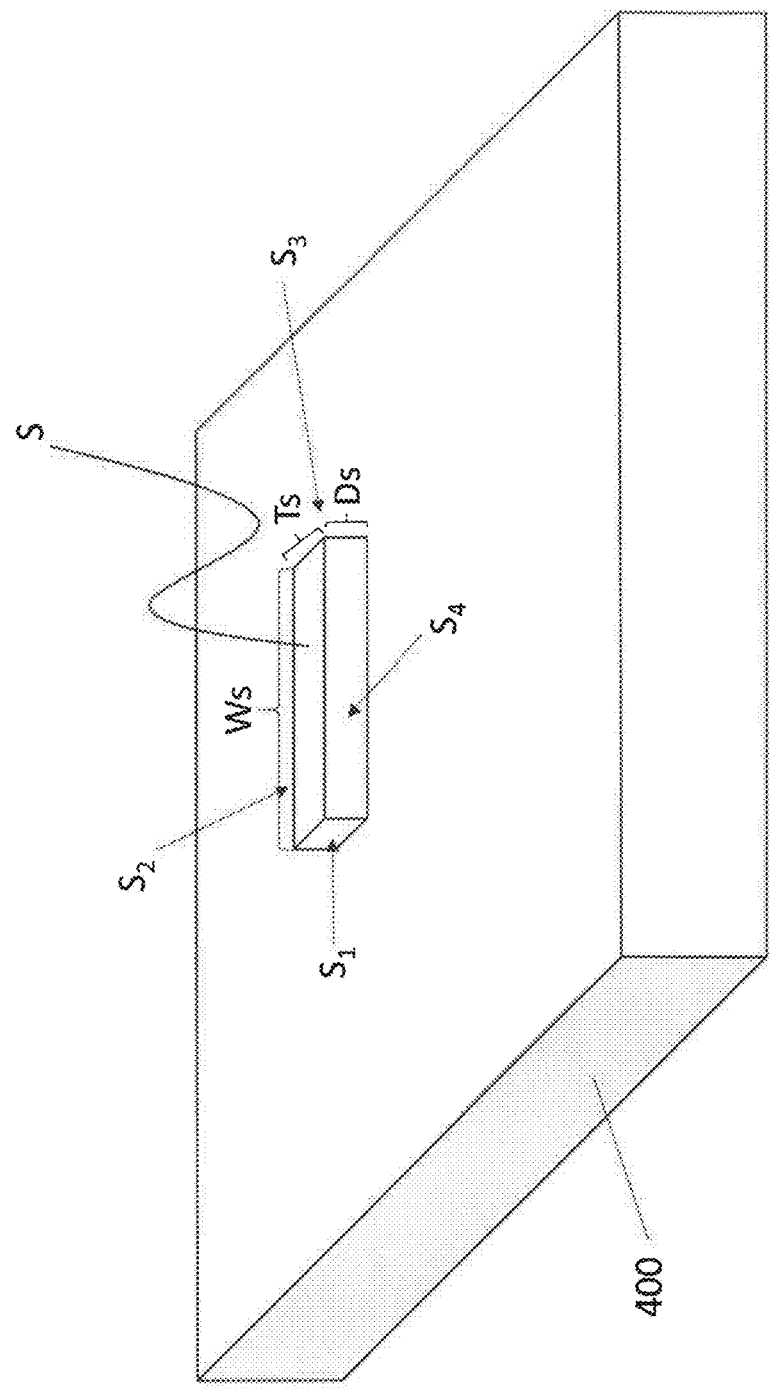
FIG. 4 illustrates the TEM sample 5, according to an exemplary aspect of the present invention.

FIG. 4 illustrates the TEM sample S, according to an exemplary aspect of the present invention. As illustrated in FIG. 4, the TEM sample S may be lifted out of the structure 300 by a probe and then transferred by the probe and mounted onto a carrier 400 (e.g., a TEM half-grid) while it is still in a chamber of the FIB device 210. Final FIB milling may be performed while the TEM sample S is on the carrier 400.

After the final FIB milling, the TEM sample S may, for example, have a width Ws in a range from 5 µm-10 µm, a depth Ds less than the width Ws and in a range from 2 µm-8 µm, and a thickness Ts smaller than the width Ws and the depth Ds and in a range from 50 nm to 150 nm.

The TEM sample S may then be transported out of a chamber of the FIB device 210 on the carrier 400 and placed in a chamber of the broad beam ion mill 215. The broad beam ion mill 215 may be used to mill a surface of the TEM sample S in order to remove a surface portion of the TEM sample S which has been damaged by the milling performed by the FIB device 210. That is, the broad beam ion mill 215 may be used to expose and underlying surface (e.g., a pristine surface) which has not been damaged by the FIB device 210.

In particular, the TEM sample S may include a parallel-sided sample in which case the broad beam ion mill 215 may remove a surface portion from two parallel sides of the plurality of sides $S_1$-$S_4$ of the parallel-sided sample. For example, referring to FIG. 4, the broad beam ion mill 215 may remove a surface portion (e.g., a damaged portion) from sides $S_2$ and $S_4$ which have an area of Ds×Ws. The surface portion to be removed may include a thickness in a range from 5 nm to 15 nm.

As noted above, about 1 nm of the surface of the TEM sample S may be damaged by the FIB device 210 per kV of accelerating voltage of the incident ion beam (e.g., gallium (Ga) ions). Thus, for example, where the TEM sample S is finished with 5 kV Ga ions in the FIB device 210, about 5 nm of a side (e.g., two parallel sides of the plurality of sides S1-S4) will be removed by the broad beam ion mill 215.

In another exemplary aspect, to ensure that an undamaged surface (e.g., a pristine surface) is exposed, the broad beam ion mill 215 may be configured to remove more than 1 nm (e.g., more than 1.5 nm) per kV Ga ions. For example, in this exemplary aspect, where the TEM sample S is finished with 5 kV Ga ions in the FIB device 210, about 7.5 nm of a side (e.g., two parallel sides of the plurality of sides S1-S4) will be removed by the broad beam ion mill 215.

In another exemplary aspect, the broad beam ion mill 215 may be configured so that a side (e.g., two parallel sides of the plurality of sides S1-S4) of the TEM sample S is inspected (e.g., by SEM) during the milling (e.g., continuously or periodically), and the milling is ceased upon the inspection indicating that the surface is pristine (e.g., sufficiently undamaged to provide an accurate strain measurement (e.g., greater than 0.1% strain sensitivity)). For example, the TEM sample S may be inspected after 1 nm per kV Ga ions, and if the inspection reveals that the surface is not pristine, then the broad beam ion mill 215 may mill another 0.1 nm per kV Ga ions a side, and so on, until the pristine underlying surface is exposed by the milling.

The broad beam ion mill 215 may utilize, for example, an argon ion beam having a size in a range from 0.5 µm to 1.5 µm. Further, the broad beam ion mill 215 may be operated, for example, at a current in a range from 0 µA to 300 µA and a voltage in a range from 0 eV to 2000 eV. In a particular embodiment, the broad beam ion mill 215 may be operated at a current in a range from 120 µA to 150 µA and a voltage in a range from 500 eV to 900 eV.

Referring again to FIG. 2, after the surface portion of a side of the TEM sample S (e.g., two parallel sides of the plurality of sides S1-S4 of the TEM sample 5) has been removed by the broad beam ion mill 215 to expose an undamaged underlying surface, then the milling of the broad beam ion mill 215 may be stopped, and the milled TEM sample S transported on the carrier 400 out of the chamber of the broad beam ion mill 215 and into the strain analyzer 220. The strain analyzer 220 may perform NBD analysis on the milled TEM sample S to acquire diffraction data.

Figure 5:
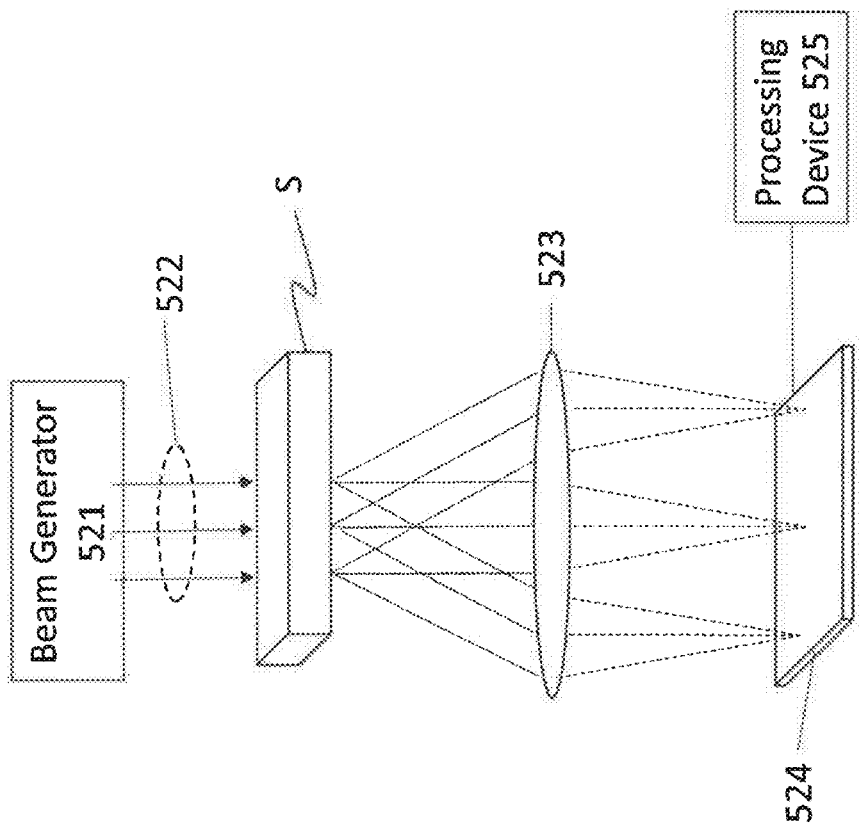
FIG. 5 illustrates a strain analyzer 520 (e.g., a TEM/NBD instrument), according to an exemplary aspect of the present invention.

FIG. 5 illustrates a strain analyzer 520 (e.g., a TEM/NBD instrument), according to an exemplary aspect of the present invention. The strain analyzer 220 may be similar in design to the strain analyzer 520. The strain analyzer 520 performs NBD analysis on the milled TEM sample S.

As illustrated in FIG. 5, the strain analyzer 520 includes a beam generator 521 (e.g., TEM unit) which generates a collimated electron beam 522. The beam size of the electron beam in NBD mode 522 may be, for example, in a range of 0.5 nm to 5 nm. The collimated electron beam 522 is scattered off the atoms in the TEM sample S.

The strain analyzer 520 (e.g., TEM) also includes an objective lens 523 through which the scattered beam is passed, onto a receiving unit 524 (e.g., charge coupled device (CCD)) which generates a diffraction pattern (e.g., diffractogram) (e.g., see FIG. 8C).

The sensitivity of the NBD technique utilized by the strain analyzer 520 may be determined by looking at the standard deviation of the NBD measurements in an unstrained region of the structure compared to the reference diffraction pattern taken from the same region of the sample. One standard deviation ($\sigma$) of this data set is accepted as the sensitivity of the technique.

Referring again to FIG. 5, the strain analyzer 520 may also include a processing device 525 (e.g., computer, microprocessor, server, etc.) which is coupled to the receiving unit 524 and processes the diffraction pattern data generated by the receiving unit 524, and output the results (e.g., as a display on a display device). For example, the results may be presented as a plot of strain as a function of position.

For example, the processing device 525 may execute a computer program (e.g., F-Strain or Epsilon) to read and fit NBD maps and profiles in standard format. The program may perform data analysis in three steps: First, each diffraction pattern is filtered using an auto-correlation algorithm. Second, an algorithm locates a number (e.g., 30) of the most inner reflections in the diffraction pattern. Third, a two dimensional grid is fitted to all (e.g., 30) spot locations, using the confidence level of each individual spot location ($\sigma_x$, $\sigma_y$) as weight in the fit of the grid.

The base vectors of the grid are then compared to vectors imported from unstrained material, and the strain is determined as $\varepsilon=(g_{ref}-g_{strain})/g_{strain}$. A special filtering feature may also be used in the analysis, which makes it possible to measure strain in semiconductor (e.g., silicon) devices even in the presence of other crystalline materials covering the probed area, which is important for the characterization of the next generation of devices (e.g., finFETs, VFETs, etc.).

NBD patterns are commonly taken at image resolutions ranging from 256 pixels$^2$ up to 2048 pixels$^2$ (2 k). The higher the number of pixels in the image, the smaller the detectable displacement of the diffraction spots which can be detected. The strain analyzer 520 of the present invention (e.g., microscope detector) may be capable of obtaining images with a resolution of 4096 pixels$^2$ (4 k). That is, the strain analyzer 520 may use a TEM camera image resolution of at least 4000×4000 pixels to acquire a diffraction pattern (e.g., diffraction data) for the milled TEM sample S.

Figure 6:
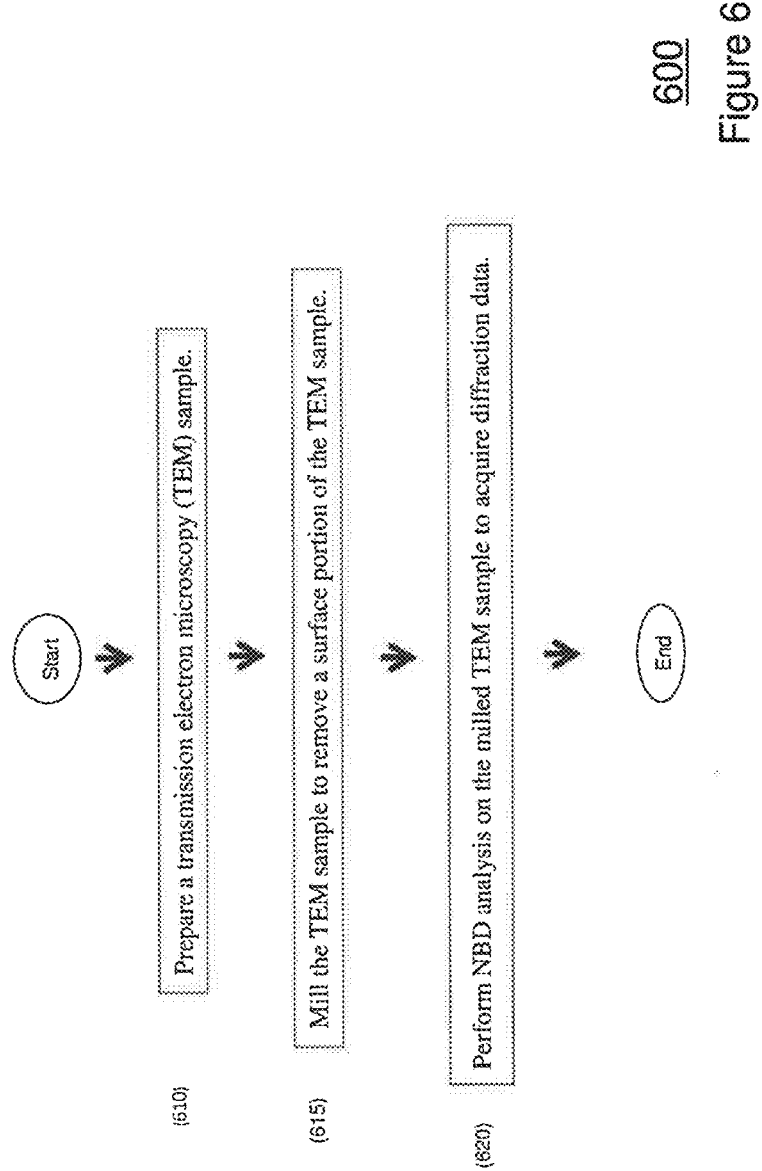
FIG. 6 illustrates a method 600 of performing nano beam diffraction (NBD) analysis, according to an exemplary aspect of the present invention.

Referring again to the drawings, FIG. 6 illustrates a method 600 of performing nano beam diffraction (NBD) analysis, according to an exemplary aspect of the present invention.

As illustrated in FIG. 6, the method 600 includes preparing (610) a transmission electron microscopy (TEM) sample, milling (615) the TEM sample to remove a surface portion of the TEM sample, and performing (620) NBD analysis on the milled TEM sample to acquire diffraction data.

Figure 7:
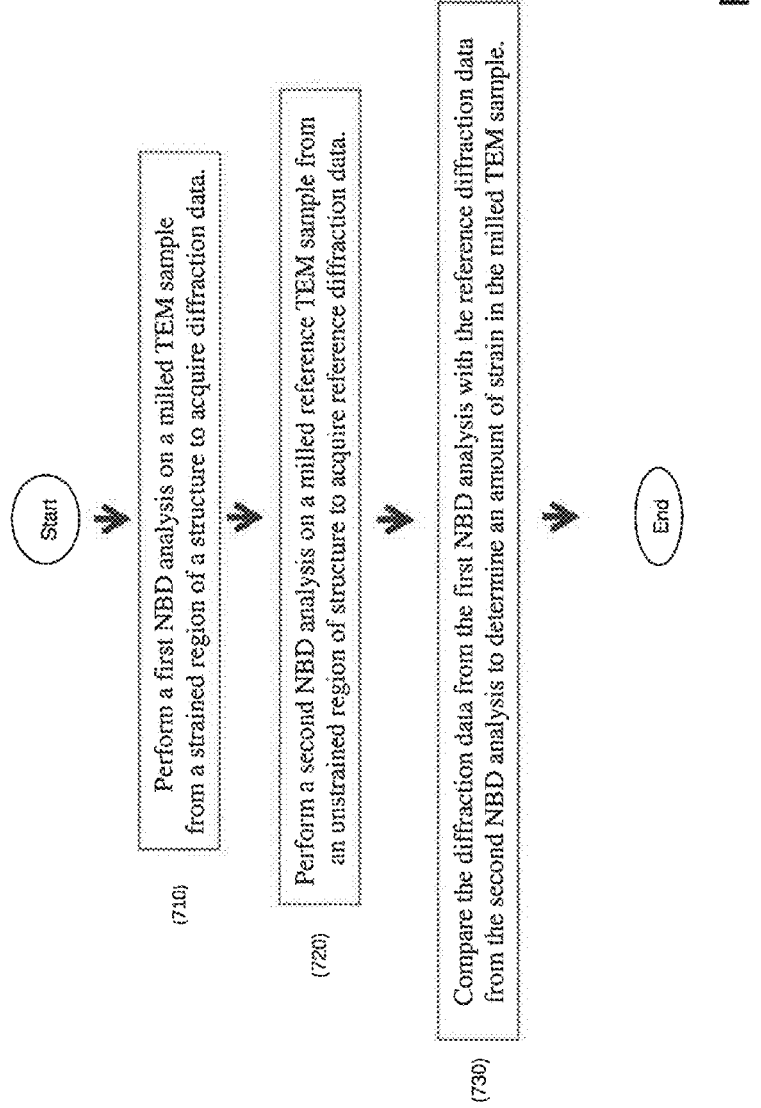
FIG. 7 illustrates a method 700 of performing strain analysis, according to an exemplary aspect of the present invention.
Figure 8:
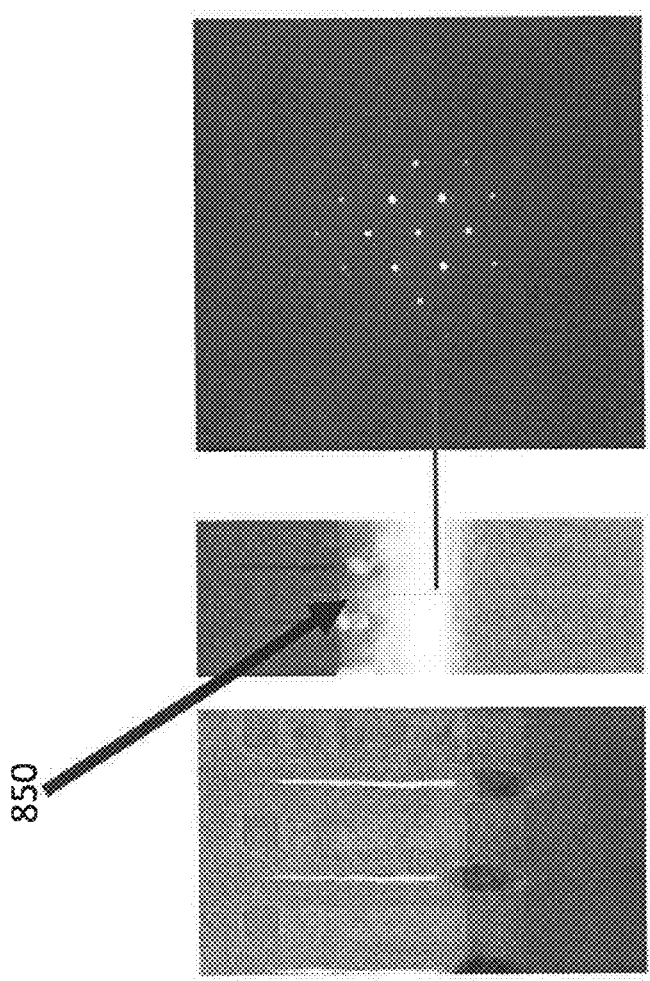
FIG. 8A illustrates a bright field TEM image of a semiconductor finFET gate (e.g., test structure), according to an exemplary aspect of the present invention.
FIG. 8B illustrates the same finFET gate as a DFSTEM image, according to an exemplary aspect of the present invention.
FIG. 8C illustrates a NBD pattern generated by the analysis on the same finFET gate illustrated in FIGS. 8A and 8B using 4 k×4 k resolution, according to an exemplary aspect of the present invention.

FIG. 7 illustrates a method 700 of performing strain analysis, according to an exemplary aspect of the present invention.

In the method 700, a diffraction pattern (e.g., one or more diffraction patterns) may be taken for a TEM sample S in a strained region of the structure 300, and a reference diffraction pattern (e.g., one or more reference diffraction patterns) may be taken in the unstrained region of the structure 300 (e.g., a single crystal region). The position of the diffraction points in the two diffraction patterns is compared. The amount of displacement of the points may be considered to be due to the stress in the strained region and, therefore, a measure of strain in the TEM sample S.

As illustrated in FIG. 7, the method 700 includes performing (710) a first NBD analysis on a milled TEM sample from a strained region of a structure to acquire diffraction data, performing (720) a second NBD analysis on a milled reference TEM sample from an unstrained region of the structure (i.e., the same structure) to acquire reference diffraction data, and comparing (730) the diffraction data from the first NBD analysis with the reference diffraction data from the second NBD analysis to determine an amount of strain in the milled TEM sample.

In the method 700, the milled TEM sample and the milled reference TEM sample may both be produced as discussed above for the TEM sample S (e.g., with the system 200). That is, for both the milled TEM sample and the milled reference TEM sample, the FIB device 210 may be used to prepare a TEM sample and the broad beam ion mill 215 may be used to mill the TEM sample to remove a surface portion of the TEM sample and produce the milled TEM sample (e.g., the milled TEM sample and the reference milled TEM sample).

EXAMPLES

The inventors have performed tests using the system 200 and methods 600, 700, and the results of these tests are provided below.

For example, in one test, a sample was made on an advanced technology node finFET test structure and analyzed in a 200 kV TEM equipped with a 4 k camera and commercially available strain analysis software using a sub 5 nm parallel probe. The data compared here was obtained on the same physical gate and as a result it was possible to align subsequent NBD scans with respect to each other to ensure the same area of the sample was being directly compared across data sets to within a few nanometers of positioning. The strain profile of the structure (not shown) exceeded 1% strain which allowed straightforward alignment of the data.

FIG. 8A illustrates a bright field TEM image of the semiconductor finFET gate (e.g., test structure), according to an exemplary aspect of the present invention. FIG. 8B illustrates the same finFET gate as a DFSTEM image. In addition, the line 850 in FIG. 8B indicates the line of analysis for acquiring NBD patterns on this sample. FIG. 8C illustrates a NBD pattern generated by the analysis on the semiconductor finFET gate illustrated in FIGS. 8A and 8B using 4 k×4 k pixel resolution, according to an exemplary aspect of the present invention.

In this test, the inventors determined that doubling the step size of the data acquisition from 5 nm per step ($\sigma=0.0753$) to 2.5 nm per step ($\sigma=0.0716$) changed in the sensitivity of the data by about 5%. It is important to note that the 2.5 nm data set contained twice the number of data points for calculating $\sigma$ compared to the 5 nm data set over the same distance in the sample. Changing the image resolution from 2 k ($\sigma=0.0867$) to 4 k ($\sigma=0.0753$) showed an improvement in the standard deviation of about 13% across 26 separate data points in each acquisition.

After the above data was obtained, the sample was thinned using a broad beam Argon (Ar) ion mill operating at 900 eV to remove the damage layer on either side of the sample. Unfortunately the sample was excessively thinned (greater than 50% reduction in thickness) during this process and the original gate of analysis did not survive intact.

An alternative gate on the same sample was analyzed instead. When the same data points in the sample were compared for $\sigma$, the pre Ar ion mill sample had a $\sigma$ of 0.0785 and the post Ar ion mill sample had a $\sigma$ of 0.0718. This is about an 8.5% improvement in $\sigma$.

As such a significant reduction in thickness of the sample could have introduced other effects (e.g. strain relaxation, significantly less diffraction events, etc.) upon $\sigma$, a second sample was fabricated and analyzed to determine if the removal of the damage layer has an impact upon $\sigma$. The second sample was reduced in thickness on the order 15%.

The 2.5 nm step size and 4 k camera resolution were used to obtain the data from the same gate in the sample for the comparison below. The before and after Ar ion milling $\sigma$s were 0.099 and 0.083 respectively showing an 18.5% improvement in $\sigma$.

Figure 9:
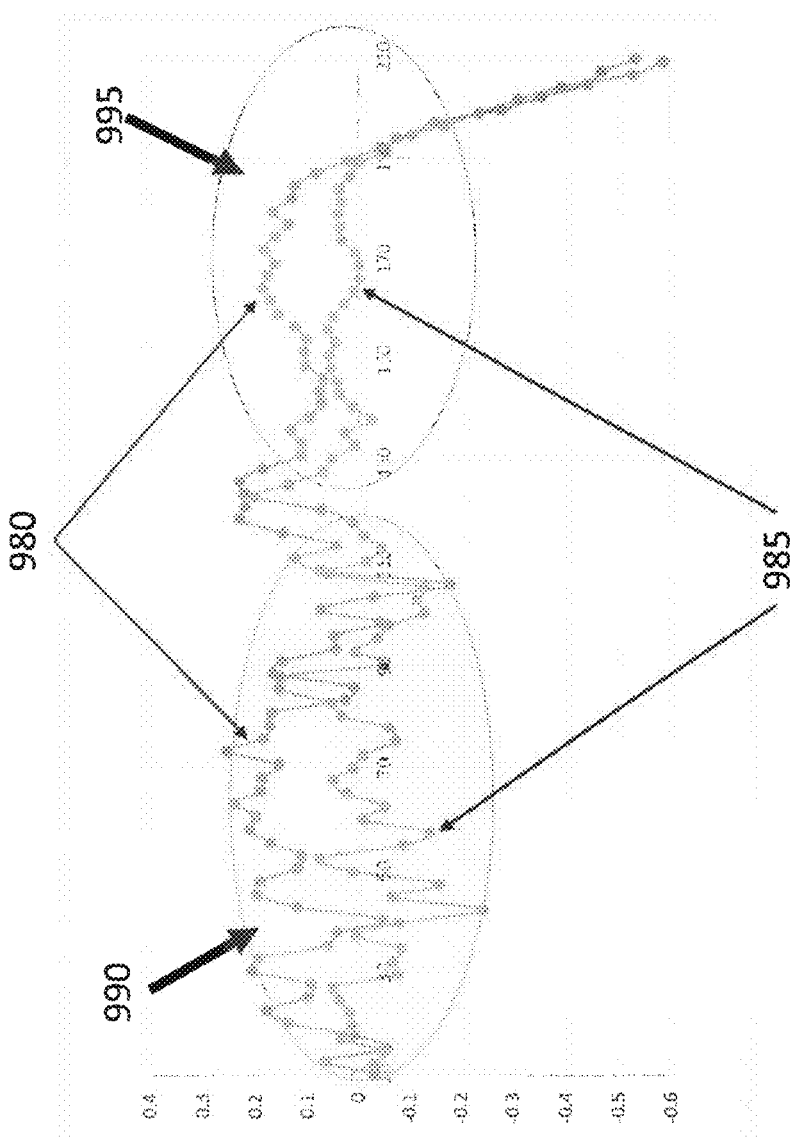
FIG. 9 provides a graph which plots the standard deviation of the NBD measurements in the tests performed by the inventors.

FIG. 9 provides a graph which plots the standard deviation of the NBD measurements in the tests performed by the inventors. Each point in the graph in FIG. 9 represents a standard deviation for 220 strain (e.g., strain in the {220} direction) obtained from a diffraction pattern of a TEM sample extracted from a structure (e.g., semiconductor structure). As noted above, one standard deviation of the data set is accepted as the sensitivity of the NBD technique.

All of the diffraction pattern images were obtained with a 4000×4000 pixel camera setting. The ordinate of the graph is the standard deviation of the diffraction pattern data obtained on the TEM sample, and the abscissa is the number of diffraction pattern images.

As illustrated in FIG. 9, the graph includes first standard deviation data 980 for TEM samples which were not milled by the broad beam ion mill (i.e., TEM samples prepared by the related art system 100), and second standard deviation data 985 for TEM samples which were milled by the broad beam ion mill (i.e., TEM samples prepared according to an exemplary aspect of the present invention). The graph also identifies a first set 990 of the data 980, 985 which was taken from an unstrained region (e.g., including a sensitivity calculation region) of the structure, and a second set 995 of the data 980,985 taken from a strained region of the structure.

As illustrated in FIG. 9, the standard deviation for the data 980 obtained for samples prepared without the broad beam ion mill was 0.0989, whereas the standard deviation for the data 985 obtained for samples prepared with the broad beam ion mill was 0.0834, indicating a significant improvement in sensitivity of strain data obtained by the NBD technique by use of the broad beam ion mill.

The various experimental parameters and their corresponding impact upon a are summarized in Table 1 below.

TABLE 1

| Experimental impact of parameters on σ | |
| --- | --- |
| Parameter | % Improvement of σ |
| Decreasing Step Size | 5 |
| Increasing Image Resolution | 13 |
| Removing Sample Surface Damage | 18.5 |

Thus, based on the tests conducted by the inventors, it was determined that oversampling the data acquisition by overlapping the NBD probe by 50% (5 nm probe with 2.5 nm steps) leads to a negligible improvement in the sensitivity of the technique. However, increasing the number of pixels of each diffraction pattern from 2 k to 4 k (e.g., at least 4 k, or 4000×4000) and removing the FIB prepared sample surface damage both show improvements in NBD sensitivity greater than 10%. As a result, it is possible to obtain greater sensitivity of the NBD technique by employing these changes in response to the evolving characterization needs.

With its unique and novel features, the present invention provides a system and method of performing nano beam diffraction (NBD) analysis which may provide diffraction data having a sensitivity which is less than 0.1%.

While the invention has been described in terms of one or more embodiments, those skilled in the art will recognize that the invention can be practiced with modification within the spirit and scope of the appended claims. Specifically, one of ordinary skill in the art will understand that the drawings herein are meant to be illustrative, and the design of the inventive method and system is not limited to that disclosed herein but may be modified within the spirit and scope of the present invention.

Further, Applicant's intent is to encompass the equivalents of all claim elements, and no amendment to any claim the present application should be construed as a disclaimer of any interest in or right to an equivalent of any element or feature of the amended claim.

What is claimed is:

1. A system for performing diffraction analysis, comprising:
    a focused ion beam (FIB) device for removing a sample from a structure;
    a mill for milling the sample to remove a surface portion of the sample; and
    an analyzer for performing diffraction analysis on the milled sample.

2. The system of claim 1, wherein the diffraction analysis comprises nano beam diffraction (NBD) analysis, the sample comprises a transmission electron microscopy (TEM) sample, the mill comprises a broad beam ion mill for milling the sample, and the analyzer comprises a strain analyzer.

3. The system of claim 2, wherein the analyzer performs the NBD analysis on the milled sample to acquire diffraction data.

4. The system of claim 3, wherein the milling of the TEM sample exposes an underlying surface of the TEM sample, and the strain analyzer uses a TEM camera image resolution of at least 4000×4000 pixels to acquire the diffraction data on the underlying surface.

5. The system of claim 3, wherein the surface portion removed by the broad beam ion mill comprises a portion of the surface of the TEM sample which has been damaged by the FIB device.

6. The system of claim 3, wherein the TEM sample comprises a parallel-sided sample, and the broad beam ion mill removes a surface portion from two parallel sides of the parallel-sided sample.

7. The system of claim 3, wherein the surface portion comprises a thickness in a range from 1 nm to 45 nm.

8. The system of claim 3, wherein the surface portion comprises at least 10% of a thickness of the TEM sample.

9. The system of claim 3, wherein the diffraction data comprises a sensitivity which is less than 0.1%.

10. The system of claim 3, wherein the broad beam ion mill is operated at a current in a range from 120 μA to 150 μA and a voltage in a range from 500 eV to 900 eV.

11. The system of claim 3, wherein the broad beam ion mill utilizes an argon ion beam having a size in a range from 0.5 μm to 1.5 μm.

12. A method of performing diffraction analysis, comprising:
    removing a sample from a structure;
    milling the sample to remove a surface portion of the sample; and
    performing diffraction analysis on the milled sample.

13. The method of claim 12, wherein the diffraction analysis comprises nano beam diffraction analysis, the removing of the sample comprises removing a transmission electron microscopy (TEM) sample, the milling of the sample comprises milling the TEM sample, and the performing of the diffraction analysis comprises using a strain analyzer to perform NBD analysis.

14. The method of claim 13, wherein the NBD analysis is performed on the milled sample to acquire diffraction data.

15. The method of claim 14, wherein the milling of the TEM sample exposes an underlying surface of the TEM sample, and the strain analyzer uses a TEM camera image resolution of at least 4000×4000 pixels to acquire the diffraction data on the underlying surface.

16. The method of claim 14, wherein the removing of the TEM sample is performed by using a focused ion beam (FIB) device, the milling of the TEM sample is performed by using a broad beam ion mill, and the surface portion comprises a portion of the surface of the TEM sample which has been damaged by the FIB device.

17. The method of claim 16, wherein the milling of the TEM sample is performed by a broad beam ion mill operated at a current in a range from 120 μA to 150 μt and a voltage in a range from 500 eV to 900 eV.

18. The method of claim 16, wherein the broad beam ion mill utilizes an argon ion beam having a size in a range from 0.5 μm to 1.5 μm.

19. The method of claim 16, wherein the TEM sample comprises a parallel-sided sample, and the broad beam ion mill removes a surface portion from two parallel sides of the parallel-sided sample.

20. A method of performing strain analysis, comprising:
   performing a first strain analysis on a sample removed from a strained region of a structure to acquire diffraction data;
   performing a second strain analysis on a reference sample removed from an unstrained region of the structure to acquire reference diffraction data; and
   comparing the diffraction data with the reference diffraction data to determine an amount of strain in the sample.

* * * * *